United States Patent [19]
Dick et al.

[11] Patent Number: 5,994,617
[45] Date of Patent: Nov. 30, 1999

[54] ENGRAFTMENT OF IMMUNE-DEFICIENT MICE WITH HUMAN CELLS

[75] Inventors: John E. Dick; Suzanne Kamel-Reid, both of Toronto, Canada

[73] Assignee: HSC Research Development Corporation, Ontario, Canada

[21] Appl. No.: 08/323,587

[22] Filed: Oct. 17, 1994

Related U.S. Application Data

[63] Continuation of application No. 07/454,193, Dec. 21, 1989, abandoned, which is a continuation-in-part of application No. 07/409,154, Sep. 19, 1989, abandoned.

[30] Foreign Application Priority Data

Sep. 19, 1988 [GB] United Kingdom .................. 8821922

[51] Int. Cl.$^6$ ............................ C12N 15/00; A61K 35/00
[52] U.S. Cl. ............................. 800/8; 424/93.1; 424/529; 424/573; 424/577
[58] Field of Search .................................. 800/2, DIG. 5; 424/9, 520, 573, 577

[56] References Cited

U.S. PATENT DOCUMENTS 5,476,996  12/1995  Wilson et al. ............................... 800/2

OTHER PUBLICATIONS

Cesano et al., Homing and Progression Patterns of Childhood Acute Lymphoblastic Leukemias in Severe Combined Immunodeficiency Mice, Blood, vol. 77, No. 11 (Jun. 1), 1991:pp. 2463–2474.

Sawyers, et al., Propagation of Human Blastic Myeloid Leukemias in the SCID Mouse, Blood, vol. 79, No. 8 (Apr. 15), 1992:pp. 2089–2098.

Lozzio, et al., Brief Communication: Human Myelogenous (Ph$^1$+) Leukemia Cell Line: Transplantation Into Athymic Mice, Journal of National Cancer Institute, vol. 56, No. 3, Mar. 1976.

Reddy et al., Human Lung Tumor Growth Established in the Lung and Subcutaneous Tissue of Mice with Severe Combined Immunodeficiency, Cancer Research 47, 2456–2460, May 1, 1987.

Fodstad et al., Lack of Correlation between Natural Killer Activity and Tumor Growth Control in Nude Mice with Different Immune Defects, Cancer Research 44, 4403–4408, Oct. 1984.

Zietman et al., A Comparative Study on the Xenotransplantability of Human Solid Tumors Into Mice with Different Genetic Immune Deficiencies, Int. J. Cancer: 47, 755–759 (1991).

Fischberg et al., Colony Formation on Spleens of Irradiated Mice Injected with Human Marrow Cells, Session III, Experimental Hematology, Biology Division Oak Ridge National Laboratory, No. 13:1967.

Mosier et al., Transfer of a Functional Human System to Mice with Severe Combined Immunodeficiency, Nature, vol. 335, Sep. 15, 1988.

Huppes et al., Acute Human vs. Mouse Graft vs. Host Disease in Normal and Immunodeficient Mice, Eur. J. Immunol., 197–206 (1992).

Mond, et al., Role of the Thymus in Directing the Development of a Subset of Lymphocytes, J. Exp. Med., vol. 155, Mar. 1982, 924–936.

Kamel–Reid, et al., Bone Marrow From Children in Relapse with Pre–B Acute Lymphoblastic Leukemia Proliferates and Disseminates Rapidly in scid Mice, Blood, vol. 78, No. 11 (Dec. 1);pp. 2973–2981.

Lapidot, et al., Cytokine Stimulation of Multilineage Hematopoiesis from Immature Human Cells Engrafted in SCID Mice, Science, Reprint Series, Feb. 28, 1992, vol. 255, pp. 1137–1141.

Guyer, This Week In Science: Scid Mice and Childhood Leukemia, Science 246: 1539 (Dec. 22, 1989).

Guyer, This Week In Science: Mouse Models and Human Diseases, Science 242: 1619 (Dec. 23, 1988).

Marx. Science: Progress Reported on Mouse Models for AIDS, Science 242: 1638 (Dec. 23, 1988).

D. Golde Sci. Amer. Dec. '91 pp. 86–93.

S. Watanabe et al. Cancer Res. 38:3494–8 (Oct. 1978).

S. Kamel–Reid Science 242:1706–9 (Dec. 23, 1988).

I. Fohlmeister et al. Nat. Immun. Cell Growth Reg. 4:221–8 ('85).

A. Wade et al. Transplantation 44(1):88–92 ('87).

Bosma et al., Nature 301: 527–530 (1983).

Reddy et al., Cancer Research 47:2456–2460 (1987).

Dare et al., J. Immunol. Meth. 85:353–361 (1985).

McCune et al., Science 241:1632–1639 (1988).

*Primary Examiner*—Bruce R. Campbell
*Assistant Examiner*—Anne Marie S. Beckerleg
*Attorney, Agent, or Firm*—Alston & Bird LLP

[57] ABSTRACT

A process for transplanting into an immunodeficient mouse, which is deficient in T-cells and B-cells, human cells to form a chimeric mouse is provided. The transplanted human cells proliferate and thereby permit in vivo study of the human cells. The human cells are isolated from a human tissue source. The process comprises:

i) irradiating an immunodeficient mouse deficient in T-cells and B-cells with radiation to condition the mouse for transplant:

ii) transplanting into the irradiated mouse, the isolated human cells; and iii) maintaining the mouse to proliferate the human cells in and permit the human cells to spread in the mouse, to provide thereby a chimeric mouse incorporating the human cells in appropriate murine tissue.

26 Claims, 6 Drawing Sheets

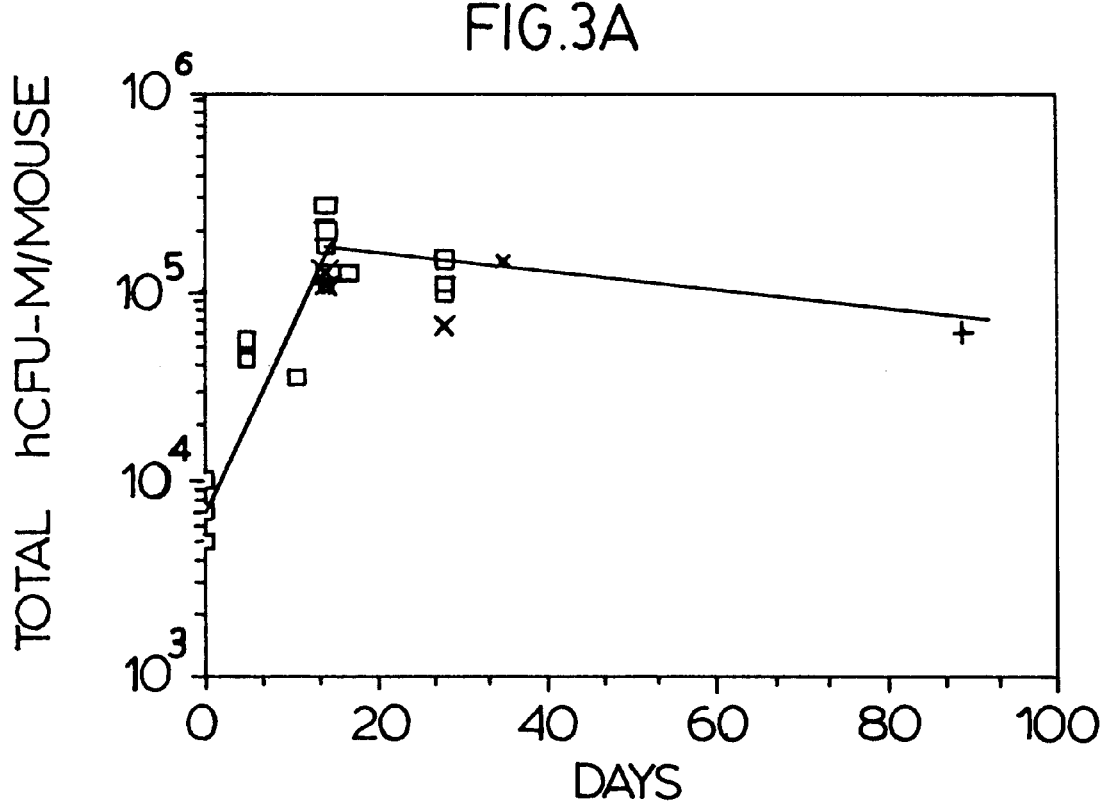
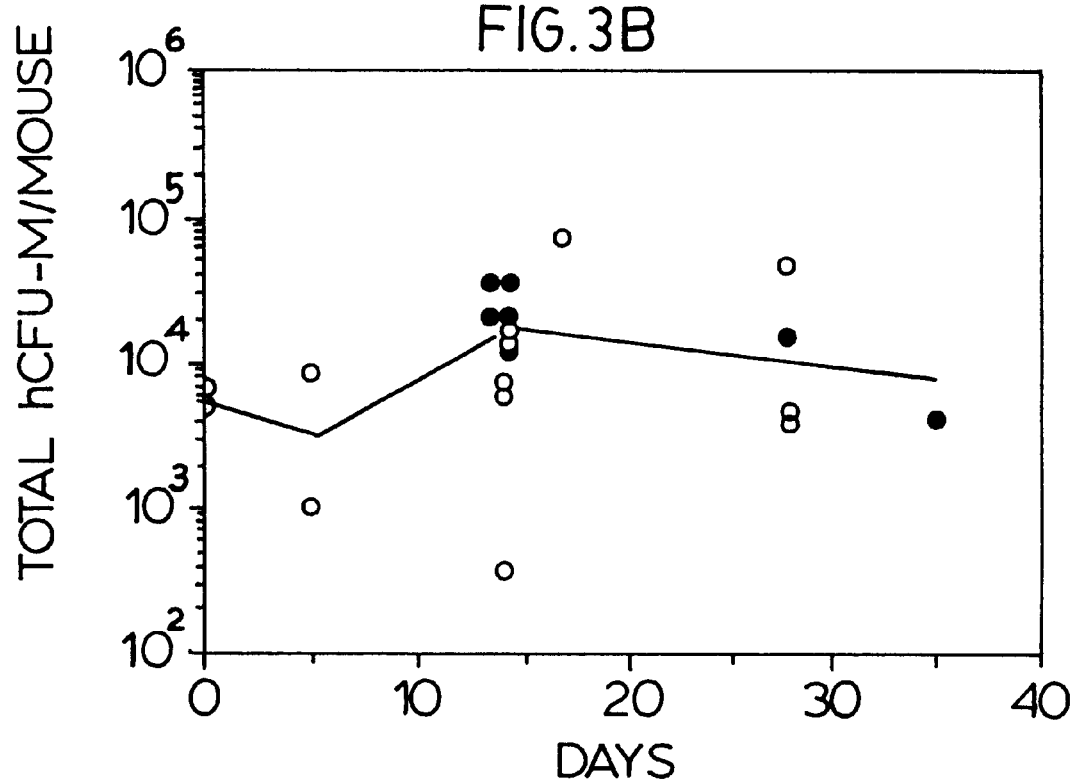

ENGRAFTMENT OF IMMUNE-DEFICIENT MICE WITH HUMAN CELLS

This is a continuation of copending application Ser. No. 07/454,193 filed on Dec. 21, 1989, now abandoned which is a continuation-in-part of 07/409,154 filed on Sep. 19, 1989 now abandoned.

FIELD OF THE INVENTION

This invention relates to transplant of immunedeficient mice with various types of human cells and the resultant mice produced by such transplant.

BACKGROUND OF THE INVENTION

Considerable investigations have been conducted in attempting to grow human calls in other animals to permit the study of such human cells. Background information is provided in several publications and many techniques which are employed in the development of this invention are also described in other publications. To facilitate reference to theme publications, the following legend is provided:

1. Till, J. E. and McCulloch, E. A., Biochem Biophys Acta 605, 431-(1980)
2. Phillips, R. A. (1985), In Ford, R. J. and Maizel, A. L. (eds), New York:Raven Press, 135.
3. Barr, R., Whang-Peng, J. and Perry, S., Science 190, 284–285 1975).
4. Dorshkind, K., Pollock, S. B., Bosma, M. J. and Phillips, R. R., J. Immunol. 134, 3798–3801 (1985).
5. Kenny, J. J., Guelde, G., Hansen, C., and Mond, J. J., J. Immunol. 138, 1363–1371 (1987).
6. Fulop, G., and Phillips R. A., J. Immunol. 136 4438–4443 (1986).
7. Waye, J. S. and Willard, H. P., Nucleic Acids Research 15, 7549–7569 (1987).
8. Erlich, H. C., Gelfand, D. H. and Saiki, R. K., Nature 331, 461–462 (1988).
9. Chervenick, P. A., Boggs, D. R., March, J. C., Cartwright, G. E., and Wintroke, M. M. Amer. J. Physiol 215, 353–360 (1968).
10. Matioli, G. Vogel, H. and Nierviseh H., J. Cellular Physiol., 72, 229–234 (1968).
11. Laneuville, P., Chang, W., Kamel-Reid, S., Fauser, A. A. and Dick, J. E., Blood 71, 811–814 (1988).
12. Dick, J. E., Magli, M.-.C., Phillips, R. A. and Bernstein, A., Trends in Genet 2, 165-(1986).
13. Dick, J. E., Magli, M. C., Huezar, D. R., Phillips, R. A. and Bernstein, A., Cell 42, 71-(1985).
14. Kindler, V., Thorens, B., DeKossodo, S., Allet, B., Eliason, J. F., Thatcher, D., Farber, N., and Vassalli, P., Proc. Natl. Acad. Sci. USA 83, 1001–1005 (1986).
15. Donahue, R. E., Wang, E. A., Stone, D. K., Kamen, R., Wong, G. G., Sehgal, P. K., Nathan D. J. and Clark, S. Nature 321, 872–875 (1986).
16. Pauser, A. A. and Messner, H. A., Blood 52, 1243- (1978).
17. D. Belpomme, J. Minowada and G. E. Moore, Cancer 30, 282 (1972).
18. S. Watanabe, Y. Shimosota, M. Kuroki, Y. Sato, T. Nakajima, Cancer Res. 40, 2588 (1980).
19. S. Kamal-Reid and J. E. Dick, Science 242, 1706 (1988).
20. M. Letarts, S. Iturbe and E. J. Quackenbush, Mol. Immunol. 22, 113 (1985); L. J. Picker, J. De Los Toyos, M. J. Telen, B. F. Haynes and E. C. Butcher, J. Immunol. 142, 2046 (1989); L. a. Goldstein et al, Cell 56, 1063 (1989); I. Stamenkovic, M. Amiot, J. M. Pesando and B. Seed, Call 56, 1062 (1989).
21. J. S. Waye and H. F. Willard, Nucleic Acids Res. 15, 7549 (1987).
22. G. A. Carlson, B. A. Taylor , S. T. Marshall and A. H. Greenberg, Immunogenetics 20, 287 (1984).
23. K. A. Foon and R. F. Todd III, Blood 68, 1 (1986).
24. C. B. Lozzio and B. B. Lozzio, Blood 45, 321 (1975).
25. A. Keating et al, in Normal and Neoplastic Hematopoieses, D. W. Golds, P. M. Marks, Eds. (Alan Liss, N. Y., 1983), pp. 513.
26. G. C. Avanzi et al, British J. Immunol., 69, 359 (1988).
27. T. Papayannopoulou, B. Nakamoto, S. Kurachi, M. Tweeddale, M. Messner, Blood, 72, 1029 (1989).
28. C. Sirard, S. Kamol-REid, J. E. Dock, unpublished results.
29. Z. Estrov, T. Grunberger, I. D. Dube, Y-P. Wang, M. H. Freedman, New Engl. J. Mod., 315, 538 (1986).
30. P. Laneuville, W. Chang, S. Kamel-Reid, A. A. Fauser and J. E. Dick, Blood 71, 811, (1988).

One area of interest is the cells of the human hematopoietic system. The mature cells within the hematopoietic system have a finite life span and are continuously being replenished by the proliferation and differentiation of lineage specific progenitor cells derived from pluripotent hematopoietic stem cells (Till, J. E. et al, supra). The knowledge of the regulation of this complex cell system, including the identification of various classes of progenitor cells, the protein factors that stimulate their growth, and the molecular events that underlie the abnormalities that occur in diseases such an leukemia, have been derived largely from the development of both in vivo and in vitro assays of the various cells within the stem cell hierarchy. Our understanding of the biology of the human hematopoietic system has suffered relative to the understanding the murine hematopoietic system of the mouse because of the lack of any type of in vivo assay system for pluripotent human stem cells (Phillips, R. A., supra and Ogawa, M. et al. supra).

Previous attempts to grow human bone marrow by direct transplantation into lethally irradiated animals have been unsuccessful (Louwagie, A. C. et al, supra). Implantation into mice of human bone marrow in diffusion chambers has been generally unsuccessful and has not provided evidence for anything more than maintenance of mature human cells for short periods of time (Barr, R. et al, supra).

It is believed that at least in theory, two major barriers may prevent growth of transplanted human bone marrow in irradiated recipient mice; presence of NK cells and absence of human hematopoietic growth factors. Lethally irradiated mice still possess enough immune function to reject the foreign cells. Even immune deficient mice, which lack functional T and B lymphocytes, such as scid and nude have high levels of NK activity which have in the past been understood to mediate a host response against the donor cells (Dorshkind, K. et al, supra and Fostad, O. at al, supra).

Another area of interest in growing human cells to permit in vivo studies is the growth of human leukemic cells. It is very difficult to grow primary human leukemia cells in culture. The difficulties suggest that there are selective processes that may result in alterations of the properties of the cells over time [Belpomme et al, *Cancer*, 30:282 (1972)]. In spite of the need for in vivo models to develop treatment strategies and an understanding of leukemic transformation and progression, very little progress has been made in the scientific community. Subcutaneous transplantation of lymphoid and mysloid cell lines, lymphomas or primary patient material into nude mice has produced myelosarcomas or localized solid tumors uncharacteristic of the primary leukemia. The growth of human leukemic cell lines in the hematopoietic tissue of nude mice has been described in Watanabe, at al *Cancer Res.* 38:3494 (1978). The developed cell line in the mouse was a highly aneuploid T-ALL cell line and was maintained in the mouse as an ascites tumor in the mouse. The animals died within two to four weeks. The growth of the human leukemic cells as an ascites or solid subcutaneous tumor in immune-deficient mice does not properly reflect the normal course of the disease as it progresses in humans. The results with human leukemic cells as with human bone marrow cells and many other types of human cells emphasize the need to be able to transplant such cells in a mouse for purposes of in

SUMMARY OF THE INVENTION

Using the techniques that have become available over the last several years, we have developed an in vivo assay by reconstituting immune-deficient mice with human cells of a desired characteristic to be studied. Molecular analysis revealed that at 14 days of reconstitution the bone marrow and spleen were chimeric with 0.5 to 1.0% of the cells being of human origin. More importantly, these tissues gave rise to large increases in the number of differentiated human macrophage progenitors (hCFU-M) over 100 days of growth in vivo, indicating seeding, proliferation and differentiation of human cells within the mouse.

According to an aspect of the invention, a process is provided for reconstituting immune-deficient mice with human cells where growth of such human cells are maintained in the appropriate cellular environment or tissue of the mouse. The process comprises irradiating the immune-deficient mice with a suitable level of radiation. Human cells are then transplanted into the irradiated immune-deficient mice and maintaining the mice in which the human cells commence replicating.

According to another aspect of the invention, a process for transplanting into an immunodeficient mouse, deficient in T-cells and B-cells, human cells to form a chimeric mouse in which the human cells proliferate is provided. The chimeric mouse permit in vivo study of the human cells, the human cells having been isolated from a human tissue source The process comprises:
  i) irradiating an immunodeficient mouse deficient in T-cells and B-cells with radiation to condition said mouse for transplant;
  ii) transplanting into the irradiated mouse the isolated human cells; and
  iii) maintaining the mouse to proliferate the human cells in and permit the human cells to spread in the mouse, to provide thereby a chimeric mouse incorporating the human cells in the appropriate cellular environment or tissue.

According to another aspect of the invention, the process is particularly suited to the transplantation of human bone marrow cells or human leukemic cells into mice. The process is particularly suited for application to "bg/nu/xid" mice or scid mice. In the bg/nu/xid mouse, the nude (nu) mutation makes the animals athymic, the beige (bg) mutation reduces the number of NK cells and the (xid) mutation reduces the lymphokine activated killer cells (LAK) an important activity in the host response to foreign cells (Kenny, J. J. et all supra). The scid mutation is deficient in T-cells and B-cells.

According to another aspect of the invention, a chimeric immunodeficient bg/nu/xid mouse or scid mouse is transplanted with human cells which proliferate and spread therein. According to a preferred aspect of the invention, the human cells may be either human bone narrow cells or human leukemic cells.

BRIEF DESCRIPTION OF THE DRAWINGS

FIGS. 3A and 3B are graphs showing the increase in bone marrow and spleen of the number of hcFU-M from transplanted mice from the time of reconstitution;

DETAILED DESCRIPTION OF THE PREFERRED EMBODIMENT

Figure 1A:
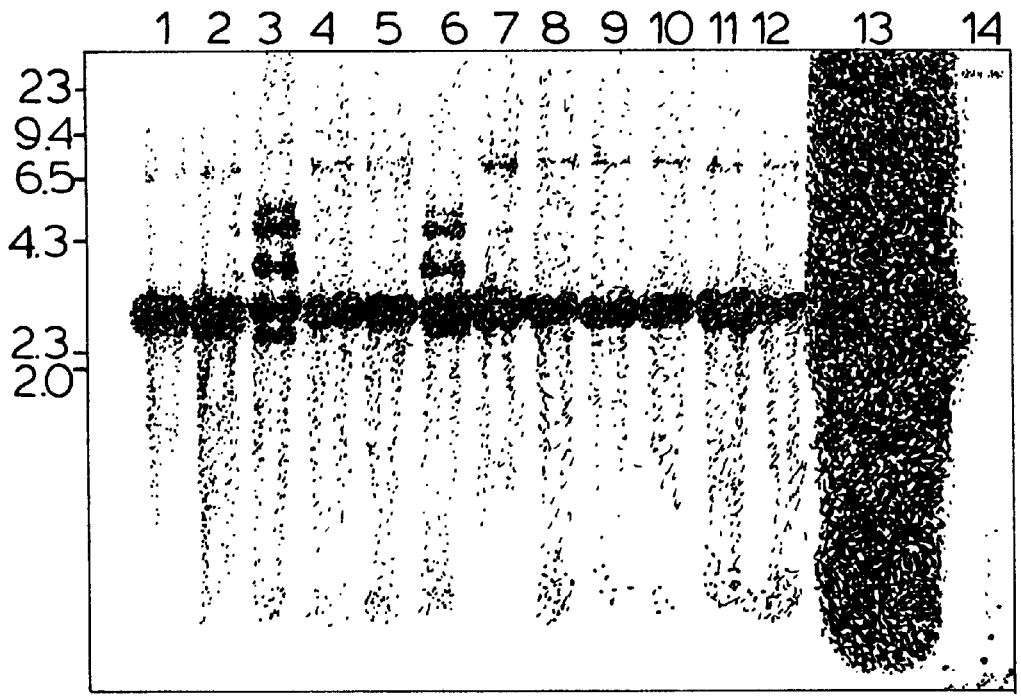
FIG. 1 (A–B) are Southern Blot analysis of bone marrow and spleen from mice reconstituted with normal human bone marrow.

According to this invention, immunodeficient mice can be successfully transplanted with a variety of human cells to provide in vivo analysis of the cell characteristics. The human cells, which are transplanted, are isolated from a human tissue source. Such sources include human blood, human bone marrow, human muscle and related material and any other form of biopsied human tissue. Transplant of this material has not been accomplished in the past so that little is known about the genes that regulate the normal differentiation and proliferation program of a variety of human cells, such as human hematopoietic stem cells. By overcoming limitations of the prior techniques, this invention provides an in vivo assay which offers enormous opportunity to study human cells in their growth and development. For example, in transplanting human hematopoietic stem cells into a mouse, one is now able to characterize the organization and developmental program of such stem cells. The mouse will also be a valuable model in which to test various gene transfer and long term expression in human cells as a prelude to human gene therapy trials. The mice provide an important system to develop other models, such as the human leukemic disease, assays for growth factors and chemotherapeutic agents and the study of human infectious diseases, for example, which affect the human hematopoietic system. Studies can now be implemented on the introduction of important growth regulatory genes including oncogenes implicated in cell proliferation and hematopoietic differentiation into normal human bone marrow. Such developments enable, for example, the creation of mouse models for chronic myelogenous leukemia (CML) and acuto lymphoblastic leukemia (ALL).

The mouse models will also enable the study of various growth factors. For example, with regard to the hematopoietic cell system, there are several growth factors acting on primitive cell types which are species specific; for example, murine IL-3 does not stimulate the growth of human multipotent progenitor cells and vice versa (Yang, Y. C. et al, supra). Therefore, human hematopoietic growth factors IL-3 smf and GM-CSF (provided by Dr. Steven Clark Genetics Institute) were continuously infused into the "bg/nu/xid" mice using an osmotic minipump available from Alza. The pumps were implanted in the mice one day before irradiation and intravenous injection of human bone marrow. As will be demonstrated later, delivery of the growth factors to encourage replication of at least the differentiated hcFU-M cells and the precursor undifferentiated stem cells in optional. Although a variety of varying degree of immunodeficient mice are available, in accordance with this invention, the immunodeficiency in the mice is in a deficiency of T-cells and of B-cells. conditioning of this type of mouse with radiation permits transplantation of human cells in a viable manner.

Consideration of a first embodiment of the invention is given to human bone marrow cells. Successful transplantation of normal mouse bone marrow into immune deficient mice requires, according to this invention, irradiation of the recipient mice. Three different radiation doses were used in the development of the transplant protocol to promote engraftment of the human cells. All "bg/nu/xid" animals given 950 cGY die by day 8. At 800 cGY, all animals survived to at least day 12, but some animals died by day 14. Since preliminary experiments showed equivalent engraftment in recipients receiving 400 and 800 cGY, all subsequent transplanted mice were exposed to 400 cGY to examine reconstitution beyond 14 days. It is understood, of course, that depending on the type of tissue transplanted, different levels of conditioning of the mouse with radiation is required. The extent of radiation exposure may range from non-lethal low doses of approximately 200 cGY up to lethal doses of 950 cGY.

Figure 1B:
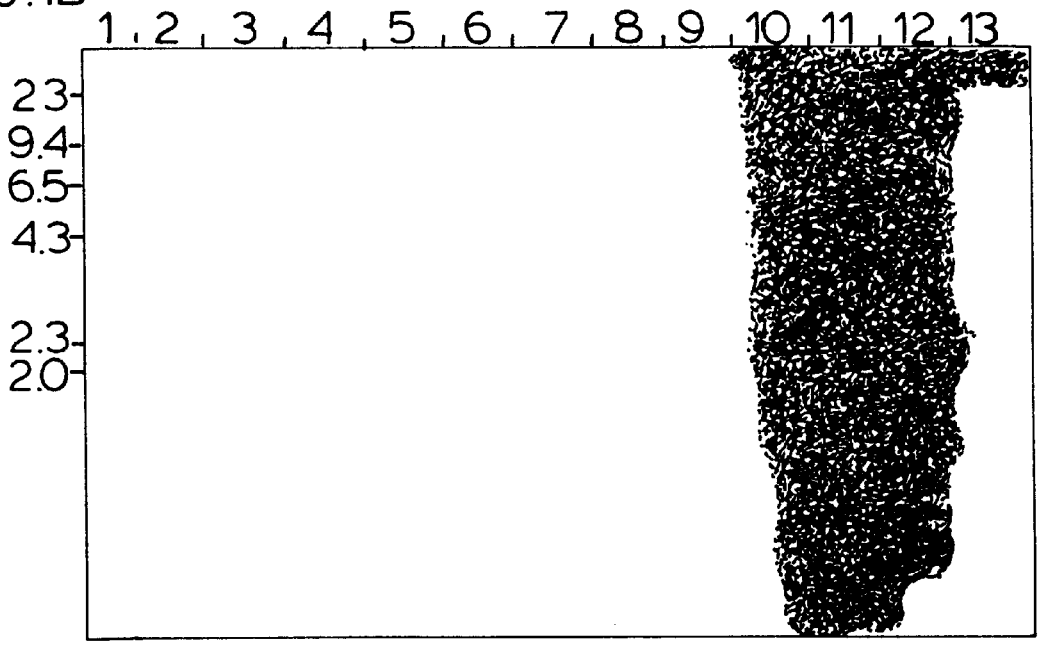

Human bone marrow is preferably isolated from a person's hip bone. The isolated bone marrow is purified to remove blood and other unwanted substitutes in accordance with normal techniques. The purified human bone marrow cells ($10^7$) were injected intravenously into CBA/J, which are not deficient in T-cells and B-cells, and "bg/nu/xid" recipients which are deficient in T-cells and B-cells; both types of recipients carry minipumps for the human hematopoietic growth factor and had been irradiated. After 14 days, the bone marrow (femora and tibia) and spleen were removed; the spleen was sectioned into five pieces. DNA from these tissue samples was analyzed by Southern blot to quantitate the proportion of human cells in the hematopoietic tissues of the recipient. The probe was a human chromosome 17 specific α-satellite probe (provided by H. F. Willard, University of Toronto, Toronto, Ontario) that does not hybridize with mouse DNA (Waye, J. S. et al, supra). As shown in FIG. 1, human DNA was detected in the bone marrow and spleen from two transplanted "bg/nu/xid" animals. The uniform intensity of the bands in the spleen sections and the bone marrow suggests that the donor cells have seeded these tissues with an even distribution rather than as discrete foci. Quantitative analysis comparing band intensities at different exposures indicates that human cells accounted for approximately 0.5 to 1.0% of the spleen and bone marrow.

We have termed these chimeric animals HID for human immune-deficient mice. No evidence of engraftment was observed in the CBA/J mice (FIG. 1B) confirming the importance of "bg/nu/xid" mice as recipients. Since the HID mice were successfully engrafted, it was important to determine whether human progenitors had also seeded to the bone marrow or spleen. Single cell suspensions of bone marrow and spleen were counted and plated in in vitro colony assays optimized for the growth of human granulocyte/macrophage (hCFU-GM) progenitor cells. Using these conditions, normal CBA/J bone marrow produces less than ton small compact colonies that die by day 8 in culture, as shown in the following Table 1.

These colonies were not counted. In contrast, HID mice (n-9 animals) contain significant numbers of progenitors that produce large diffuse colonies which remain viable for greater than 12 days in culture. The majority of Wright stained cells from individual colonies had typical macrophage morphology with high cytoplasm/nucleus ratio and foamy cytoplasm indicating that they arose from hCFU-GM or macrophage (hCFU-M) progenitor cell types. A few colonies containing either erythroid or granulocytic cell were also observed. Immune-deficient mice with growth factors but no human bone marrow did not contain any colony forming cells. CBA/J mice (n=5 animals) that received bone marrow also did not contain any human colonies; supporting the molecular evidence presented in FIG. 1 that these animals were not engrafted. Immune-deficient scid mice can also be transplanted with human bone marrow cells; however, the number of colonies is lower than with bg/nu/xid mice. It is appreciated that the number of colonies may be enhanced by use of suitable growth factors. The results of these investigations are summarized in Table 1.

TABLE 1

LEVELS OF IN VITRO COLONY FORMATION
IN BONE MARROW FROM NORMAL AND HID MICE

| Irradiated Mouse | Pump with factors | Human bone marrow | hCFU-M $2 \times 10^5$ cells | Total Bone Marrow/ Mouse | Total hCFU-M /mouse |
|---|---|---|---|---|---|
| CBA/J* | + | − | 0 | $3.1 \times 10^8$ | 0 |
| CBA/J | + | + | 0 | $2.4 \times 10^8$ | 0 |
| "bg/nu/xid" | + | + | 175⁺/−17 | $3.2 \times 10^8$ | $2.8 \times 10^5$ |
| "bg/nu/xid" | − | + | 131⁺/−64 | $3.1 \times 10^8$ | $2.0 \times 10^5$ |
| "bg/nu/xid"# | + | − | 0 | $1.8 \times 10^7$ | 0 |
| scid (2) | + | + | 9 ± 5 | $8 \times 10^6$ | 360 |

The method of engrafting the mice is as follows.

All mice received 400 cGy irradiation except as noted. Bone marrow was obtained by aspirating both femurs and tibia, counted and plated under culture conditions that support human progenitor colonies (>platen/mouse). Details of these cultures have been published (Laneuvill et al, supra and Fauser, A. A. et al, supra). Briefly, $2 \times 10^5$ cells are plated in methylcellulose, 30% human plasma, 1 U/ml erythropoietin, and 10% PHA-LCM. Most of the colonies derived from HID mice had the characteristic morphology of macrophage progenitors. The total bone marrow counts were calculated assuming that both femurs and tibia account for 19% of the total mouse bone marrow.

* not irradiated
800 cGy radiation.

Figure 2:
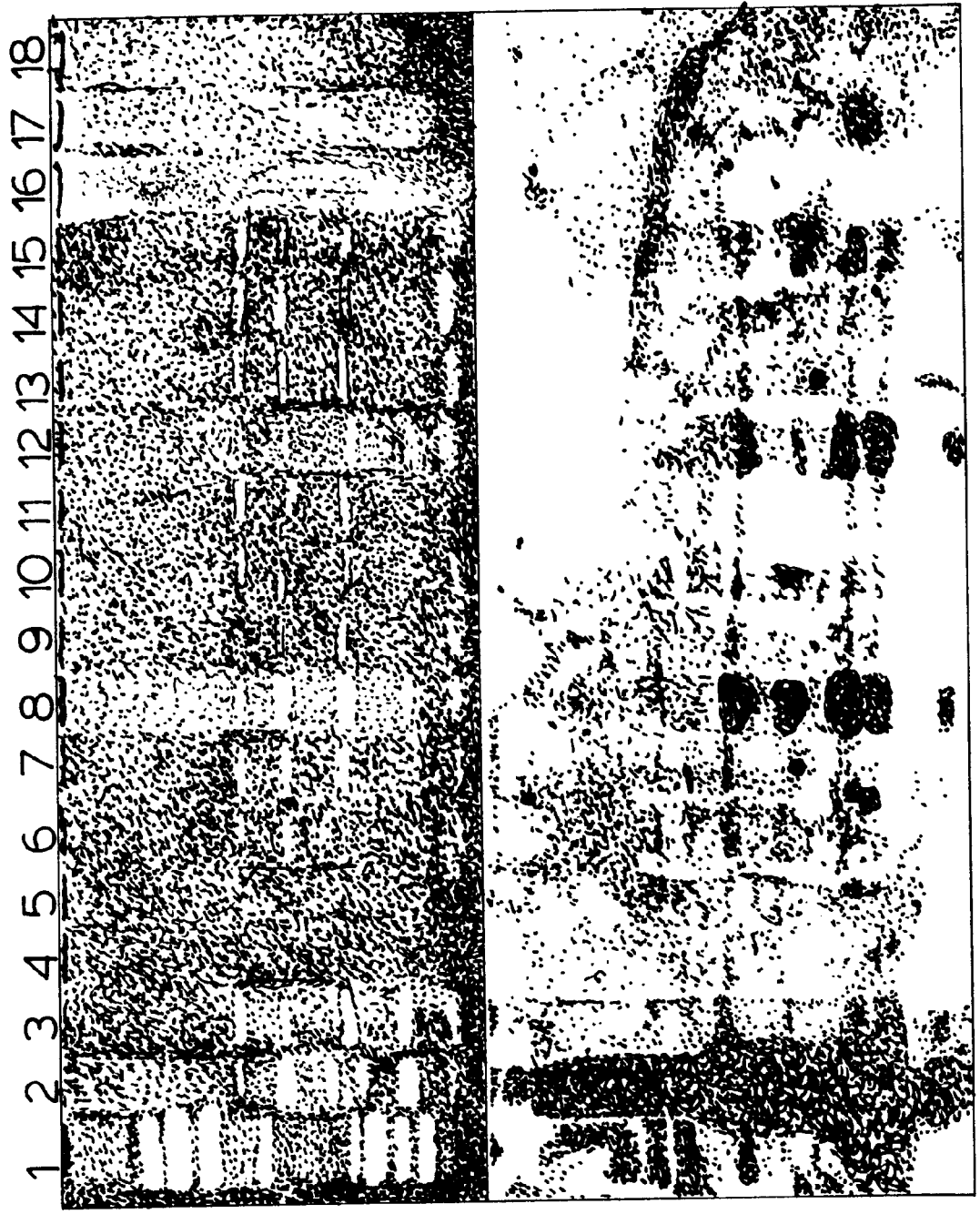
FIG. 2 is an identification by PCR analysis of human DNA in individual colonies derived from the transplanted mice.

Consistent with their human origin, the colonies that grew in the in vitro colony assays were dependent on human factors. TO obtain independent evidence that the colonies were indeed human, the polymerase chain reaction (PCR) was used to detect the presence of human chromosome 17 α-satellite DNA sequences in a single hematopoietic colony (Erlich, H. A. et al, supra). The human α-satellite sequences are composed of a family of closely related 171 bp tandem repeats. Oligonucleotide primers specific for the 5' and 3' ends of the consensus repeat sequence were used in PCR assays on individual colonies to confirm their human origin. PCR amplification of normal human DNA results in a complex pattern of bands that arise because different numbers of repeats act as templates in the PCR reaction (FIG. 2).

All the colonies picked from the plates derived from two HID mice transplanted with bone marrow from the same donor contain the same pattern of amplified bands while no amplification products were seen in the PCR reactions that contained mouse cells alone. These reactions were deliberately carried out using up to $10^4$ fold excess of mouse DNA to ensure there was no possible background amplification. PCR analysis of colonies derived from three additional HID mice in inependent experiments were also positive for human DNA. Two spleen samples from CBA/J mice that had received human bone marrow gave no detectable amplification supporting our previous conclusion that no engraftment occurred in these animals. The human identity of these bands was confirmed by Southern blot analysis of the amplified products using the a satellite probe. Only the lanes with bands hybridized, no signal was seen in the mouse lanes. Lanes 3 and 4, which contain faint bands, were is reactions done with small colonies. This data provides conclusive molecular identification of the in vitro colonies as human in origin.

If the number of progenitors detected at day 14 arose by differentiation from more primitive precursors the number of hCFU-M should increase at increasing times after transplantation. The total number of hCFU-M in the bone marrow of the mouse was calculated by counting the number of bone marrow cells in both femurs and tibia. These bone account for 19% of the bone marrow in a mouse (Chervenick, P. A. et al, supra). The total number of hCFU-M in the spleen was calculated from the total splenocyte count. FIGS. 3A and 3B show the results of six independent experiments comparing the total number of hCFU-M in the bone marrow and spleen of "bg/nu/xid" recipients between days 5 and 100. The animals received between $5-10 \times 10^6$ normal human bone marrow cells as noted in the legend. The "0" time point indicates the total number of hCFU-GM transplanted. Studies in the mouse have found that the seeding efficiency of transplanted cells into the bone marrow and the spleen is considerably less than the input number (<10% Matioli, et al supra). Therefore, the actual number of human progenitors seeding the bone marrow or spleen is certainly lese than indicated in the Figure and the calculations of the population increase are only a minimuw estimate of the true value. The total hCFU-M in the bone marrow of the day 5 animal rose >18 fold over the input number. By day 14, the number had risen >40 fold to $2.8 \times 10^5$. This level of engraftment was further maintained for a total of 3 months as shown. The minipump war estimated not to deliver growth factor beyond day 14, so the animal at day 17 was probably not receiving human growth factors. It is theorized that the necessary growth factors are being produced by cells which accompany the bone marrow transplant. Interestingly, the kinetics of engraftment of the spleen followed a different pattern, only low levels of hCFU-M were detected at day 5 and 14 but there was significant 8 fold increase at day 17. This difference may reflect delayed seeding of the spleen from the bone marrow.

Experiments have also been carried out to determine the importance of exogenously supplied human growth factor. The mice identified by the closed circle or an "x" either received no minipump or a minipump with saline (FIG. 3). The animal shown with open circle open boxes contained similar levels of hCFU-M than the animals receiving human growth factor, indicating that delivery of hematopoietic growth factors IL-3 and GM-CSF is not absolutely required for the production of hCFU-M. This result suggests either that the mice produce factor(s) that act on human stem cells or that the human cells themselves are producing their own growth factors. It is appreciated that other growth factor combinations may be used to increase the level of engraftment.

According to another embodiment of the invention, human leukemic cells were transplanted into immunodeficient mice in accordance with the method of this invention. Non-T-ALL is the most prevalent childhood lukemia and is characterized by a pre-B cell phenotype. A cell line was established from the peripheral blood of a patient undergoing a terminal relapse of non-T-ALL. The cell line was established in accordance with standard techniques. For example, a cell line was isolated and identified as an A-1 cell line which is phenotypically HLA-DR$^+$, CD19$^+$, CALLA$^-$ (CD10) and CD20$^-$No cytoplasmic or surface immunoglobulin can be detected, it has one rearranged $\mu$ chain gene while the immunoglobulin light chain genes are in the germ line configuration characteristic of a pre-B cell line. The A-1 line is EBV free, has a normal karyotype, and grows autonomously producing an unidentified factor (not IL-1,2, 3,4,5,6, G-CSF, GM-CSF) which augments its growth in semi-solid clonogenic assays and suspension cultures.

Scid mice, which are deficient in T-cells and B-cells, were irradiated with 400 cGY [Fulop, G. M. and Phillips, R. A., supra] prior to intravenous (IV) or IP injection of $10^7$ A-1 cells. At four weeks, the bone marrow and spleen were analyzed by flow cytometry for the presence of A-1 cells by determining the proportion of CD44$^+$ cells. CD44 is a cell surface proteoglycan implicated in lymphocyte homing and lymphocyte-endothelial cell interactions [Letarte, M. et al, supra; Goldstein, L. A. et al supra; Stamenkovic, I. et al supra] and is expressed at high levels on A-1 cells. The bone marrow of four scid mice injected intravenously contained 17%, 17%, 47% and 86% CD44$^+$ A-1 cells. In contrast, scid mice injected intraperitonealy contained no detectable CD44$^+$ cells in the bone marrow or spleen at this time.

Figure 4:
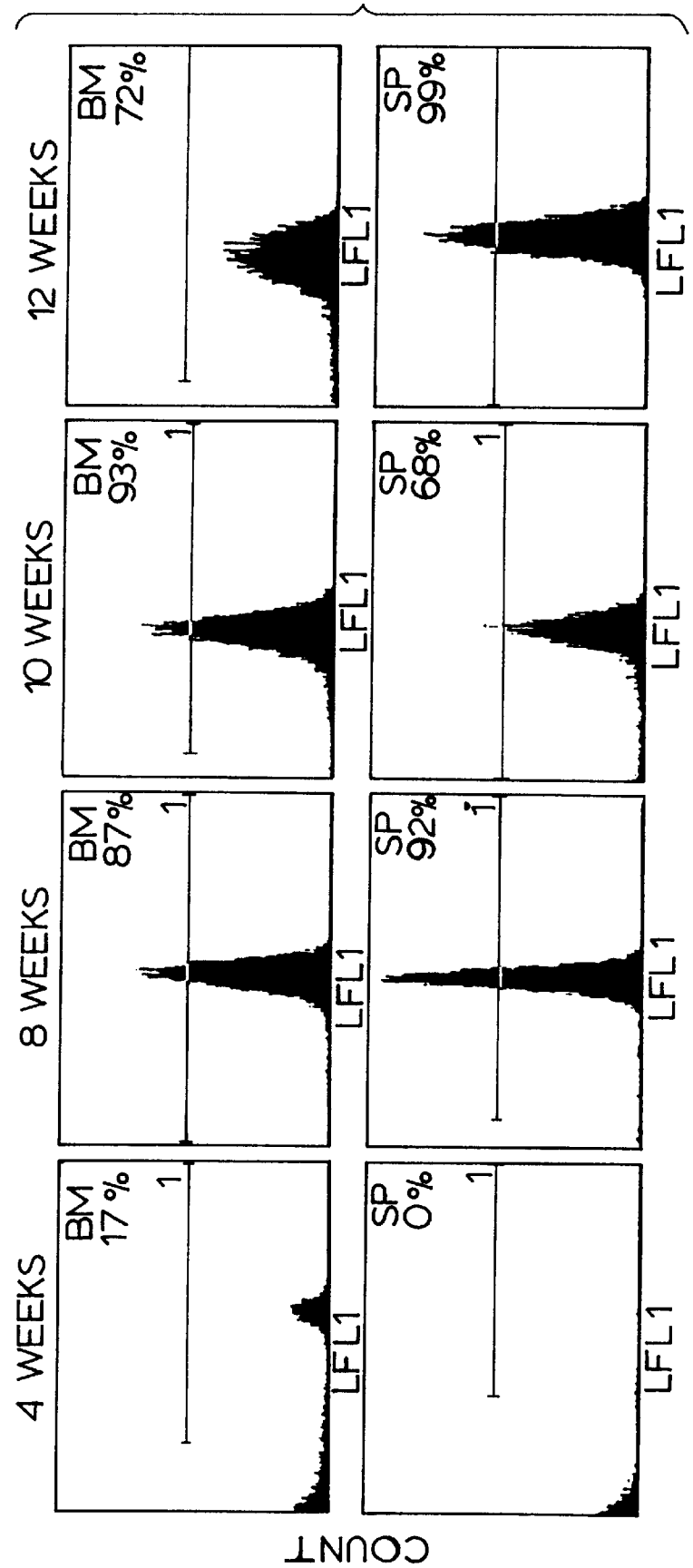
FIG. 4 is a series of graphs showing the results of flow cytometry analysis of bone marrow and spleen from scid mice transplanted with the A-1 leukemia cell line.

Examination of scid mice by flow cytometry at various times after injection of $10^7$ A-1 cells showed a pattern of infiltration reminiscent of that observed in many children with ALL. A representative series of mice is shown in FIG. 4. At four weeks post-transplant, the bone marrow contained 17% CD44$^+$ cells, while no positive cells could be detected in the spleen. After eight weeks, the proportion of A-1 cells in the bone marrow rose to 87% and the spleen contained 92% A-1 cells. This high percentage of human cells in the bone marrow and spleen was maintained in the animals analyzed at ten and twelve weeks after engraftment. Histopathological examination revealed that at eight weeks post-transplantation the interstitial regions between the kidney tubules and the peri-portal regions of the liver contained small infiltrates of A-1 cells; no leukemic cells were observed in brain, lung, intestine, heart, or pancreas (FIG. 5, only kidney, liver, brain and lung shown). At ten weeks A-1 cells were identified in the blood and the leukemic infiltrates filled most liver sinusoids and the interstitial regions and peri-renal fat of the kidney. Infiltrates were now observed in the peri-bronchial regions of the lung, in the stomach mucosa, and in the choroid plexus of the brain. After twelve weeks, infiltrates were seen in the kidney, liver, brain, lung, intestine and pancreas, reflecting a widely disseminated leukemia (FIG. 6; intestine and pancreas data not shown). The appearance of A-1 cells in the blood at ten weeks coincided with infiltration of other peripheral tissues such as lung and brain. The animals began to die at twelve weeks post-transplant.

Figure 7:
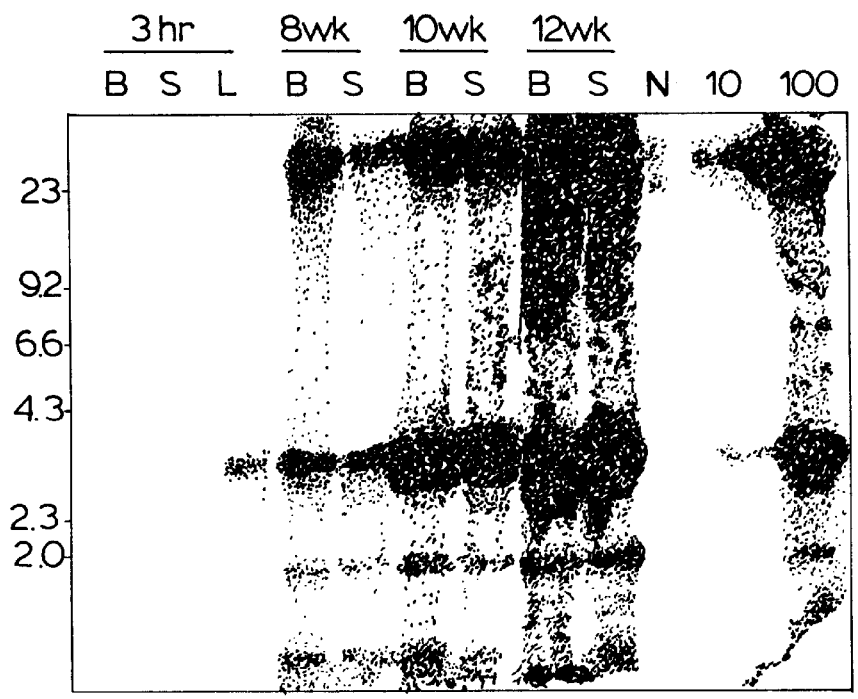
FIG. 7 is a DNA analysis of the hematopoietic tissues from the scid mice transplanted with the A-1 cells.

To obtain independent evidence of engraftment, DNA was prepared from bone marrow and spleen and the proportion of human DNA was estimated on Southern blots using the human specific chromosome 17 α-satellite probe [Waye, J. S. and Willard, H. F. supra]. As shown in FIG. 7, the bone marrow and spleen from animals sacrificed at 8, 10 and 12 weeks contained a strongly hybridizing 2.7 kb band charaateristics of the human chromosome 17 α-satellite sequence. Comparison with control lanes containing mixtures of mouse and human DNA indicated that these tissues contained between 20% and 100% human cells, consistent with the data in FIG. 4. DNA was also analyzed from the bons marrow, spleen and lung of animals sacrificed 3 hours after IV injection of A-1 cells as shown in FIG. 7. Even with long exposure times, human DNA could only be detected in the lung indicating a very low fraction of IV injected cells seeded to the hematopoietic tissues; as demonstrated previously, the majority of IV injected hematopoietic cells are trapped initially in the lungs and liver [Carlson, G. A. et al., supra].

Cell suspensions of bons marrow, spleen and peripheral blood harvested at each time point were placed in liquid cultures and assayed for colony formation as sensitive methods by which to detect A-1 cells. Large numbers of colony-forming A-1 cells were found in the bone marrow at all time points, while colonies or growth in liquid culture could only be detected in the spleen beginning 8 weeks after the engraftment (Table 2).

TABLE 2

| Weeks post Transplant | % CD44+ Cells | | | A-1 Colonies per 1 × 10⁵ Cells Plated | | |
|---|---|---|---|---|---|---|
| (No. mice) | BM | SPL | PBL | BM | SPL | PBL |
| Control (n = 6) | 0 | 0 | nd | 0 | 0 | 0 |
| 4 (n = 5) | 34* | 0 | nd | 400** | 0 | 0 |
| 8 (n = 4) | 90*** | 61**** | nd | 2000, nd | 370, tn | 0 |
| 10 (n = 2) | 86, 93 | 58, 68 | nd | tn, tn | tn, tn | tn, tn |
| 12 (n = 2) | 72, 35 | 97, 99 | nd | nd | nd | nd |
| 13# (n = 2) | 99, 99 | 75, 79 | 93 | nd | nd | nd |

\* = median of: 17, 17, 34, 47, 86%
\*\* = counts from the pooled BM of two aniamls
\*\*\* = Median of: 76, 87, 93, 95%
\*\*\*\* = median of 53, 92, 63, 58%
- These animals received 50 × 10⁶ cells by IV injection.

Colony-forming A-1 cells were detected in the peripheral blood at 10 and 12 weeks; blood smears also had detectable leukemic blasts at these time points (data not shown). Animals injected with 50×10⁶ cells were sacrificed 13 weeks after transplantation, A-1 cells constituted 90% of their bone marrow and spleen and 93% of the nucleated cells in peripheral blood (Table 2 above). The results suggest that blasts expand first in the bone marrow, subsequently migrate to the spleen and appear in the peripheral blood at the time of the onset of infiltration into other tissues such as lung and brain; analogous to the spread of non-T-ALL in children.

To determine the effects of the growth of human leukemic cells on the normal hematopoiesis, the levels of normal murine myeloid progenitors in the spleen and bone marrow of animals at 4 and 8 weeks post-transplant were measured. After 4 weeks, there was a 20-fold reduction in the number of mouse granulocyte-macrophage progenitors in the bone marrow, while the spleen contained 5-fold higher numbers of progenitors than normal controls. As shown in FIG. 4 and Table 2, only the bone marrow contained detectable A-1 cells at 4 weeks suggesting that the inhibitory effect is local because the progenitors in the spleen are not reduced. The increased numbers of progenitors in the spleen may be related to the observation that splenic hematopoiesis is elevated in mice whose bone marrow is suppressed as a consequence of irradiation. No mouse progenitors could be detected in the spleen or bone marrow from scid mice analyzed 8 weeks post-transplant, suggesting that the leukemic cells growing in these tissues either displaced or suppressed normal murine hematopoietic progenitors.

Figure 8:
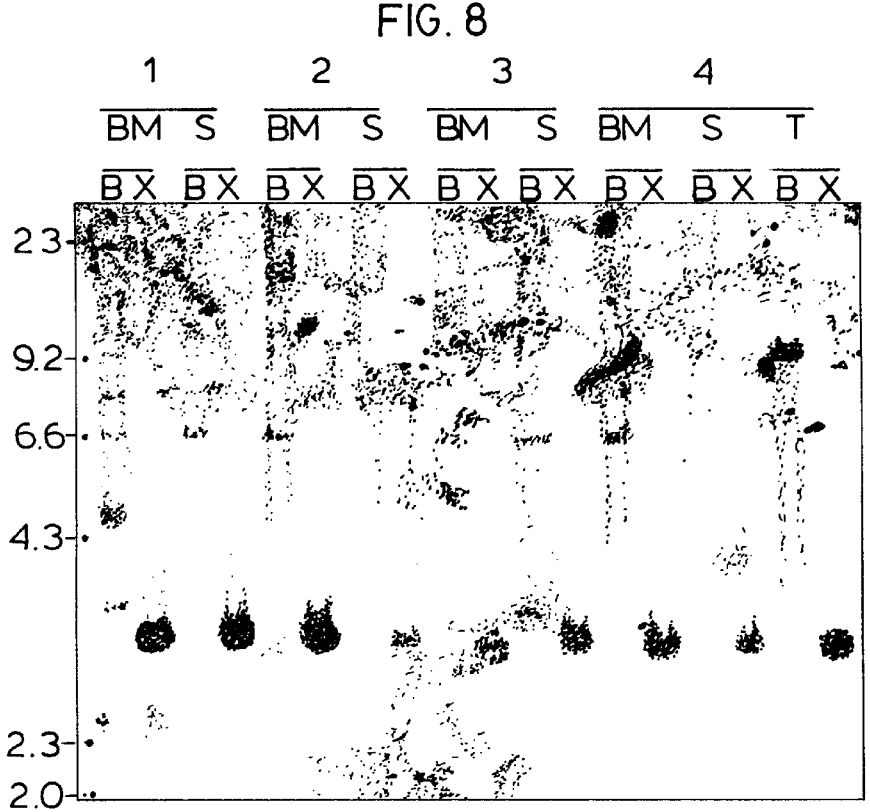
FIG. 8 is a DNA analysis of the bone marrow and spleen of scid mice transplanted with A-1 cells as infected with the PA 317-N2 retrovirus vector.

An important problem in cancer biology is understanding the clonal evolution that occurs during the spread of neoplastic growth [P. C. Nowell, Sem. Oncol. 16:116 (1989)]. Retrovirus mediated gene tranfer provides a powerful tool to carry out a clonal analysis because the retrovirus integration site uniquely marks each infected cell [J. E. Dick at al, Cell 42:71 (1985); G. Keller at al, Nature 318:149 (1985); I. Lemischka et al, Cell 45:1917 (1986); R. Snodgrass at al EMBO J. 6:3955 (1987)]. A-1 cells were infected with a retrovirus vector that contained the dominant selectable neo gone using the protocol we developed for human bone marrow [P. Laneuville et al, Blood 71:811 (1988)]. This procedure entailed cocultivatling A-1 cells for 24 hours over an irradiated nomolayer of PA317-N2 fibroblasts producing amphotropic neo virus and selected for 14 days in 200 γf/ml G418. Uninfected A-1 cells died during this selection. The infected cells were then transplanted into scid mice as described above. DNA was prepared from the bone marrow and spleen of animals 6 and 7 weeks after transplantation with infected cells (FIG. 8). Digestion or DNA with Xbal, which produces a common 3.8 kb provirus band independent of the vector integration site, indicated that the bone marrow and spleen contained a substantial proportion of infected A-1 cells. Digestion of DNA with BamH1 produces a unique sized neo containing band for each infected cell. All lanes showed a light DNA smear indicative of multiple clones and a few more prominent bands with ≦10% of the intensity of the provirus band. One common clone was present in the bone marrow and spleen of different animals while other clones were unique to one tissue such as the five clones seen n the bone marrow from animal 1. Animal 4 contained a small tumor growing near the kidney that arose from a clone different from those seen in the bone marrow and spleen. These data indicate that by six weeks some clones proliferate much faster than others; in the case of the clone common to different animals, this selection must have occurred in vitro while for other clones it occurred in vivo. It will be particularly interesting to use this approach to follow leukemic cell infiltration in to the peripheral tissues.

The ability to transplant bone marrow directly from patients with leukemia, either before or after treatment, into scid mice could be a valuable tool for predicting the clinical course of the disease, detecting residual leukemias, and for developing individualized therapeutic strategies. Toward this objective, we injected bone marrow cells from three patients with Non-T-ALL into scid mice using protocols developed for the A-1 cell line. All three patients belong to non-T-ALL group III according to immunological classification [Foon, KA. et al supra], although Patient 1 expresses low levels of CD10 and may be a more immature phenotype. The proportion of human cells in the bone marrow and spleen were analyzed by flow cytometry, colony assay, and DNA analysis by Southern blot and the polymerase chain (PCR). Table 3 indicates that in all three cases, human cells were detected in the bone marrow and spleen of the engrafted animals. Animals transplanted with bone marrow from Patient 1 still contained human cells at 7 weeks after transplant although at lower levels than at 4 weeks. No human cells could be detected in the animals transplanted with bone marrow from Patients 3 after 16 weeks. In addition to DNA analysis and flow cytometry, leukemic blast colonies were grown from the bone marrow and spleen of engrafted animals. Thus by three independent criteria, it is clear that bone marrow obtained directly from patients with leukemia can be engrafted into scid mice. It will now be important to examine the engraftment of bone marrow from a large number of patients for longer periods of time to determine whether different patterns of growth in scid mice reflect important biological parameters that correlate with clinical outcome.

TABLE 3

| | | Bone Marrow | | | Spleen | | |
|---|---|---|---|---|---|---|---|
| Patient | Time (weeks) | FC | DNA | Colonies/ $10^5$ cell | FC | DNA | Colonies/ $10^5$ cells |
| 1 | 4 | + | + | 185 | + | + | 60 |
|   | 7 | +/- | +/- | 82 | + | + | 94 |
| 2 | 4 | + | ++ | 30 | - | +/- | nd |
|   | 10 | nd | + | 68 | +/- | + | 30 |
| 3 | 9 | - | nd | 10 | + | +/- | 10 |
|   | 16 | - | - | 0 | - | nd | 0 | symbols represent the percentage human cells as determined by flow cytometry (FC), or the percentage of human DNA. For FC: ++0.10%, +6–10%, +/–1–5%, –<1% For DNA: ++>10%, +1–10%, +/–0.1–1%, –0.1%

A Similar met of experiments ware carried out in grafting or transplanting A-1 cells into bg/nu/xid (bnx) mioe. As with the scid mice, A-1 cells proliferated in the mice in the same manner that the A-1 cells proliferated in the scid mice.

The growth of A-1 cells in culture, like that of most non-T-ALL cells, requires a yet unidentified autocorine growth factor(s). The ability of A-1 cells to grow in scid and scid mice indicates that these mice may provide the factors and microenvironment necessary for A-1 cell growth, or that the transplanted cells can produce their own growth factors. Thus, we expect that cells derived from many cases of non-T-ALL leukemia may proliferate in one or both of these immune-deficient hosts, especially if the appropriate growth factors(s) were provided either by increasing the cell number administered or by providing growth factors exogenously. We have successfully engrafted other leukemic cell lines into immune-deficient mice including the myeloid lines K562 [Lozzio, C. B. et al, supra], and EM-2 [Keating, A. et al, supra], the megakaryocytic line MO7-E [Avanzi G. C, et al supra] and the erythroid line OCI-M2 [Papayannopoulou, T. et al., supra], indicating that these mice may support the growth of many types of human leukemic cell lines [Sirard, c. et al, supra]. See Table 4 of Example 10.

EXAMPLE 1

Southern blot analysis of bone marrow and spleen from animals reconstituted with normal human bone marrow was conducted as follows. Mice received $1.4 \times 10^4$ U of Il-3/day/ mouse and $1.3 \times 10^3$ U of GM-CFS/day/mouse by continuous infusion with an Alzet osmotic minipump implanted subcutaneously. This amount of factor is similar to that demonstrated to affect hematopoiesis in monkeys and mice (Kindler, V. et al, supra and Donahue, R. E. et al, supra). Mice were given 400 cGy of radiation from a Cesium source 24–48 hours after implantation of the pump. Immediately after irradiation, each mouse received $7–10 \times 10^6$ normal human bone marrow cells by tail vein injection. The mice were maintained for a desired length of time before sacrifice for analysis. DNA was extracted from bone marrow and spleen after sectioning the spleen into 5 pieces. The DNA was digested with EcoR1, blotted according to standard procedures and probed with p17H8 a human α-satellite probe specific for sequences on chromosome 17 (Waye, J. S. et al, supra). EcoR1 digestion of human DNA produces a characteristic 2.7 kb band in addition to minor bands that vary different individuals.

With reference to FIG. 1, A: DNA from HID mice 14 days (lanes 1 to 6) and 17 days (lanes 7 to 12) after transplantation with human bone marrow. Lanes 1 and 7: bone marrow; Lanes 2–6 and 8–12: spleen pieces; Lane 13: human DNA Lane 14: mouse DNA.

B: Southern analysis of spleen DNA from CBA/J mice 7 to 10 days after transplantation with human bone marrow. All mice were treated as described except that radiation dose was raised to 950 cGy in an attempt to improve engraftment. Lanes 1 and 2: spleen 10 days post transplant; Lanes 3–5: spleen 7 days post transplant; Lanes 6–9: spleen 7 days post transplant; Lanes 10–12: mixtures of human and mouse DNA lane 10, 50:50; lane 11, 30:70; lane 12 1:99 and lane 12, MW marker.

EXAMPLE 2

Identification by PCR analysis of human DNA in individual colonies from methylcellulose cultures derived from HID mice was conducted as follows. Single colonies were carefully picked from methyloellulose cultures that had been established from HID bone marrow. The colonies were lysed, treated with proteinase K and subjected to 30 rounds of PCR (Cetus). Two oligonucleotide primers specific to the 5' and 3' ends of the 171 bp repeat consensus sequence of the α-satellite ware used. The sequences of these primers were:

sense, ACGATTCTCAGAAACTTCTTTGTGAT;

antisense, TTTTATATGAAGATATTCCC.

The top panel of FIG. 2 shows an enthidium bromide stained agarose gel following electrophoresis of the products of the PCR reaction. The lower panel of FIG. 2 shows a Southern blot of the agarose gel, probed with a the P17H8 probe as described in FIG. 1. Lane 1: φX174; lane 2: 500 ng human DNA; lanes 3–15 individual hematopoietic colonies from methylcellulose cultures derived from two HID mice. Lanes 16–17 spleen DNA from CBA/J mice described in FIG. 1; and lane 18: mouse DNA.

EXAMPLE 3

Increase in the number of hCFU-M from HID mice with time of reconstitution was analyzed. The number of hCFU-M were measured in mice that had been reconstituted for the length of time indicated in FIGS. 3A and 3B. Total hCFU-M were calculated as described in Table 1. Each point represents the number of hCFU-M from the bone marrow and spleen of one animal reconstituted for the length of time indicated. The lines were fitted by eye to indicate the trend in the data. Each point represents the number of hCFU-M from the bone marrow (FIG. 3A) and spleen (FIGS. 3B) of one animal reconstituted for the length of time indicated. The lines were fitted by eye to indicate the trend in the data. These data represent 5 independent experiments using bone marrow from five different human donors. The animals denoted by the (x) or the (·) contained either no or a pump with saline.

The results presented here clearly demonstrate successful engraftment of "bg/nu/xid" mice with adult human bone marrow. A large proportion of the engraftad cells are progenitors capable of giving rise to macrophage colonies in vitro. The kinetics indicate that the bone marrow and to a lessor extent the spleen can produce large numbers of hCFU-M; at 14 days of reconstitution there was a greater than 40 fold increase in hCFU-M over the number known to be injected. Since in vitro progenitors have little self-renewal potential (Till, J. E. et al, supra), this large increase implies an earlier progenitor or stem cell has seeded the bone marrow and spleen and is responsible for producing the hCFU-M.

Although the nature of the cell giving rise to the hCFU-M is unknown, these data provide a foundation for the first in vivo human stem cell assay in a small animal. Since ws have previously achieved high efficiency gene transfer into human progenitor cells with retrovirus vectors (Laneuville, P. at al, supra), the random site of retrovirus integration may be used as a molecular marker to carry out a clonal analysis of the organization of the human hematopoietic system similar to our previous studies in which murine stem cells tagged with a retrovirus vector were followed after bone marrow transplantation [Dick, J. E. at al, supra (16) and Dick, J. E. et al, supra (17)]. The HID mice will also be a valuable model in which to test gone transfer and long-term expression in human hematopoietic cells as a prelude to human gene therapy trials. Furthermore, the HID mice may prove to be an important system to develop models of human leukemic disease, assays for growth factors and chemotherapeutic agents, and in the study of human infectious diseases that affect the hematopoistic system. In addition, it is understood that this process may be applied to transplanting other types of human cells into this type of mice to provide in vivo analysis of such human cell growth and behavior. Other human tissue includes liver cells and central nervous system cells. Such transplanted mice would therefore be very useful in stage 1 drug testing, such as in cancer chemotherapy, AIDS drugs, hematopoietic growth factors and any other drugs which affect the hematopoietic blood system.

EXAMPLE 4

In vitro colony formation of A-1 leukemic cells from scid mice was conducted (See Table 2). Animals wore transplanted with A-1 cells as described with respect to FIG. 4. The scid mice were irradiated (400c Gy) from a cesium source and immediately given $1 \times 10^7$ A-1 cells by tail vein injection. At the times indicated, the bone marrow, spleen, and peripheral blood from the transplanted scid mice were stained with 50B4 and analyzed by flow cytometry. Single cell suspensions were prepared from bone marrow and spleen. Bone marrow cells were washed two times with PBS while spleen cells were fractionated through a Percol gradient. $5 \times 10^5$ cells were stained with the 50B4 monoclonal antibody which reacts with human CD44 antigen and does not cross-react with murine cells. Washed cells were then incubated with FITC-F(ab)'$_2$ goat antibodies to mouse immunoglobulin C, washed and analyzed by flow cytometry using the Epics Profile Analyzer made by Coulter Electronics. Calls were also plated in methylcellulose cultures to quantitate the number of colony-forming cells. Briefly, $2 \times 10^5$ were plated in methylcellulose, 10% fetal calf serum, and 10% A-1 conditioned medium; colonies were scored after 14 days.

EXAMPLE 5

Engraftment of bone marrow from patients with non-T-ALL into scid mice. All three patients belong to non-T-ALL group III defined as $CD10^+$, $CD19^+$, $CD20^-$, $HLA-DR^+$ (Foon, K. A. supra). Bone marrow cells ($10^7$) were transplanted into scid mice as described with respect to Table 2. At the times indicated the proportion of human cells in the bone marrow and spleen cells was quantitated by three methods; flow cytometry to determine the percentage of CD44, CD19 or HLA-DR positive cells (these markers were expressed at high levels on the original patient cells); DNA analysis for the presence of human $\alpha$-satellite sequences; and plating in semisolid cultures to determine the number of leukemic blast colony forming cells. The DNA analysis was carried out using either the Southern blot outlined in FIG. 7 or by PCR to detect human $\alpha$-satellite sequences as previously described [Kamel-Reid, S. et al *Science* 242:1706 (1988)].

EXAMPLE 6

Flow cytometry analysis of the bone marrow and spleen from scid mice transplanted with the A-1 leukemic cell line. The scid mice bred in our defined-flora colony (Ontario Cancer Institute) were irradiated (400cGY) from a cesium source and immediately given $1 \times 10^7$ A-1 cells by tail vein injection. Animals were sacrificed at 4 week intervals and single cell suspensions were prepared from bone marrow and spleen; bone marrow cells were washed two times with PBS while spleen cells were fractionated through a Percoll gradient. $5 \times 10^5$ cells were stained with the 50B4 monoclonal antibody which reacts with human CD44 antigen and does not cross-react with murine cells. Washed cells were then incubated with FITC-F(ab) '2 goat anti-mouse IgL, washed and analyzed by flow cytometry using the Epics Profile Analyzer (Coulter Electronics). Histograms, as shown in FIG. 4, represent the cell count in each channel (Y) with a given log fluorescence intensity (X). Each panel is the date from one mouse; replicate mice gave similar results, summarized in Table 2.

EXAMPLE 7

Figure 5:
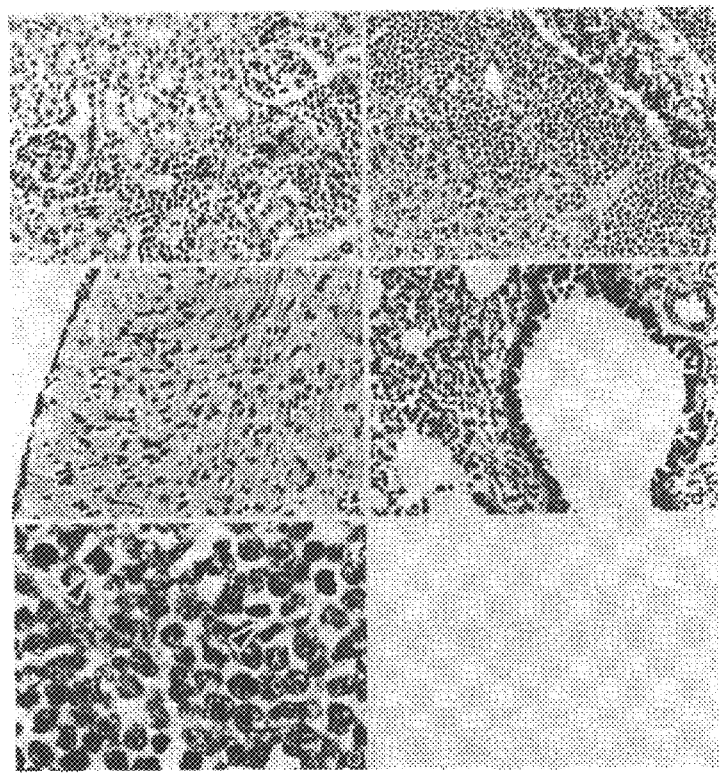
FIG. 5 (panels A–E) shows tissue sections of kidney (panel a), liver (panel b), brain (panel c) and lung (panel d) of scid mice transplanted with A-1 cells after eight weeks. Panel e is a 100×magnification of a section of panel b.
Figure 6:
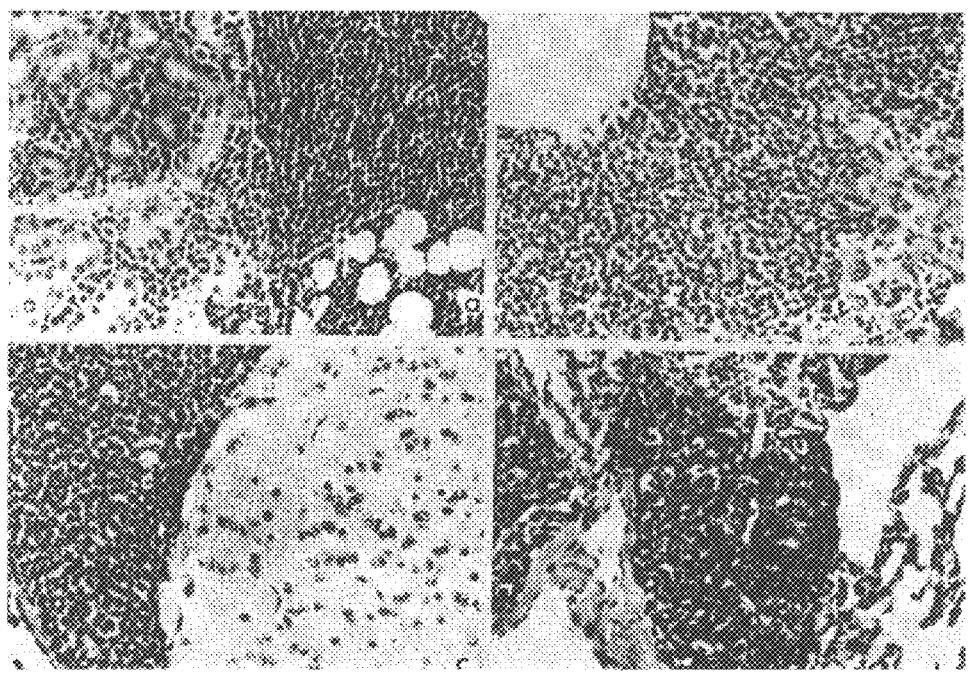
FIG. 6 (panels A–D) shows tissue sections of kidney (panel a), liver (panel b), brain (panel c) and lung (panel d) of scid mice transplanted with the A-1 leukemic cells after twelve weeks.

Histological analysis of scid mice 8 weeks after transplantation with the A-1 leukemic cells is shown in FIG. 5. Tissue sections were obtained from the kidney (panel a), liver (panel b) brain (panel c) and lung (panel d) of scid mice transplanted with A-1 cells as described in FIG. 1. The tissues wore fixed in 10% formalin, paraffin embedded, and four micron sections were cut and stained with hematoxylin and eosin. Microscopic evaluation indicated that there was a light leukemic infiltration in the interstitial region between the tubules in the kidney (a) and in the peri-portal regions of the liver (b). Note the normal hepatocytes in the lower left hand corner of (b). No leukemic cells were observed in the cerebral cortex or meninges of the brain (c) or in the peri-bronchial region of the lung (d). Magnification is 40×. Panel (e) is a 100× magnification of leukemic blasts an observed in the liver. Note the frequent mitotic figures (arrows) and homogenous cell population with atypical nuclei and a high nuclear/cytoplasmic ratio.

EXAMPLE 8

Histological analysis of scid mice tissues 12 weeks after transplantation with the A-1 leukemic cells is shown in FIG.

6. Tissue sections from the kidney, liver, brain and lung from transplanted scid mice were fixed and stained as described in the legend of FIG. 2. Panel (a) is a transverse section of the kidney with a heavy leukemic infiltration in the interstitium (left hand side) and peri-renal fat (right hand side). Panel (b) is a section through the liver demonstrating a much heavier portal infiltrate than at a weeks. Few normal hepatocytes are seen (lower right), and blasts can be seen throughout the liver tissue. Panel (c) is a section through the cerebral cortex demonstrating a dense infiltration of the meninges by leukemic cells. Panel (d) shows an example of a nodular aggregate of leukemic cells, adjacent to pulmonary vasculature, in the peri-bronchial region of the lung.

EXAMPLE 9

DNA analysis of the hematopoietic tissues from scid mice transplanted with A-1 cells. DNA was extracted from the bone marrow (B) and spleen (S) of the scid mice (shown in FIG. 7) 8, 10 and 12 weeks after transplantation with A-1 cells. In addition, DNA was also extracted from the bone marrow, spleen, and lungs (L) of scid mice 3 hours after injection or A-1 cells. DNA (2 $\mu$g) was digested with Eco R1, blotted according to standard procedures, and probed with P17H8, a human $\alpha$-satellite probe specific for human chromosome 17 [Waye at al supra]. Eco R1 digestion of human DNA produces a characteristics 2.7 kb band, in addition one third of people have polymorphisms that give rise to a series of lower molecular weight minor bands [Kamel-Reid, S. supra]. N is the negative control, 10 represents 10% human; 90% mouse DNA, and 100 represents 100% human DNA. The autoradiograph was exposed for 7 hours, except for the 3 hour lanes which were exposed for 3 days. Molecular size markers indicated in kilobases.

EXAMPLE 10

Engraftment of a variety of human leukemic cell lines in immune-deficient scid mice were conducted. Mice were irradiated as described in Example 5 and transplanted with $10^7$ cell by tail vein injection. After 4 weeks, the animals were sacrificed and the bone marrow and spleen were plated in methylcellulose cultures. Table 4 summarizes the extent of engraftment of several mgloid cell lines. Since the cultures contained only 10% FCS or human IL-3 (for Mo7E), there is was no growth of murine cells.

TABLE 4

| Cell Line | Colonies/$10^5$ Cells | |
|---|---|---|
| | Bone marrow | Spleen |
| K562 | 50 | 0 |
| EM-2 | 150 | 2 |
| EM-3 | 154 | 0 |
| M07-E | 358 | 26 |
| OCI-M2 | 1000 | 380 |

EXAMPLE 11

DNA analysis of the bone marrow and spleen of scid mice transplanted with A-1 cells infected with the PA317-N2 retrovirus vector was conducted, the results of which are shown in FIG. 8. DNA was extracted six weeks (animals 1 and 2) and seven weeks (animals 3 and 4) after transplant. DNA (5 $\mu$g) from the spleen (S), bone marrow (BM) and tumor (T) was digested with Xbal (X) or BamH1 (B), and analyzed by Southern blot using a neo specific probe. Xbal cuts once in each LTR to produce a 3.8-kb provirus band characterized of N2 while BamH1 cuts once in the provirus outside the neo gene and is flanking cellular sequences to generate band sizes that are unique to the site of integration. Molecular sizes are indicated in kilobases in FIG. 8.

The establishment of an in model for the most common form of childhood leukemia presents a unique system in which to address experimentally a number of biological questions governing the clinical outcome and the growth of leukemic cells In vivo. For example, the identification of leukemic cells in bone marrow usually dictates the course of chemotherapy; however, histological methods for detecting low numbers of residual cells are neither sensitive nor precise. While recently report in vitro assays for leukemic cells may improve both the sensitivity and precision of detecting residual leukemia [Estrov, Z. et al, supra], further refinement of the animal model described here could also offer a sensitive method by which to study residual cells from patients undergoing chemotherapy.

The ability to grow leukemic cells in immune-deficient mice provides the opportunity to develop novel treatment strategies. For example, now chemotherapeutic and immunotherapeutic protocols, combinations of biological response modifiers, or new unconventional therapies that are difficult to develop and evaluate by human experimentation can be tested in an in vivo situation which mimics the progression of human leukemia. Using high efficiency gene transfer technology [Laneuville, P et al, supra] individual leukemic cells could be marked to follow the growth and development of clones during the multistage progression of the disease. Gene transfer in conjunction with our modal eyetoa should allow the introduction of key growth regulatory genes, such as oncogenes or tumor suppressor genes, to determine how their aberrant expression affects normal hematopoiesis and leukemic transformation and progression.

It is further understood that, in accordance with this invention, other types of human cells can be transplanted and grown in a mouse in accordance with this invention. This enables the development of various mouse models to study the human cells in vivo. Other types of human cells, which are transplantable and proliferate in immunodeficient mice treated in accordance with this invention, are various carcinomas, various sarcomas, various lymphomas and as already noted, various leukemias and normal human cells such as bone marrow cells.

Although preferred techniques for transplanting the human bone marrow cells and human leukemic cells is intravenously, it is appreciated that other transplant techniques may be used depending upon the type of tissues to be transplanted. For example, carcinoma cells as isolated in colon cancer tissue can be transplanted by implanting the tissue in the peritoneal cavity or colon of the mouse. Engraftment procedures may be used for other types of carcinomas; e.g. skin cancers. Hence the transplant technique is to some extent, determined by the type of isolated tissue cells.

Although preferred embodiments of the invention have been described herein in detail, it will be understood by those skilled in the art that variations may be made thereto without departing from the spirit of the invention or the scope of the appended claims.

We claim:

1. A process for making a chimeric mouse, comprising:
  i) irradiating an immunodeficient mouse which is deficient in both T-cells and B-cells before irradiation treatment to condition said mouse for transplant to permit human cell engraftment in said mouse;

ii) transplanting human hematopoietic cells comprising human hematopoietic stem cells by intravenous injection into said irradiated mouse; and iii) maintaining said mouse to allow said human hematopoietic stem cells to engraft in at least murine bone marrow tissue and function by proliferating to produce progenitor cells differentiate into mature hematopoietic progeny.

2. The process of claim 1, wherein said step of irradiating said mouse comprises exposing said immunodeficient mouse to approximately 200 cGY to 950 cGY of radiation.

3. The process of claim 2, wherein said immunodeficient mouse is exposed to approximately 400 cGY.

4. The process of claim 1, wherein said immunodeficient mouse is a bg/nu/xid mouse.

5. The process of claim 1, wherein said immunodeficient mouse is a mouse bearing the SCID mutation.

6. The process of claim 1 wherein approximately $10^3$ to $10^8$ human cells are injected intravenously into said irradiated mouse.

7. The process of claim 1, wherein growth factors are administered to said mouse during step (iii).

8. A process of claim 7 wherein hematopoietic growth factors are administered to said mouse during step (iii).

9. A process of claim 1 wherein the hematopoietic cells are bone marrow cells.

10. The process of claim 1, wherein said human hematopoietic cells are isolated from the group consisting of human bone marrow, human peripheral blood, human cord blood, and human fetal liver.

11. A chimeric immunodeficient mouse transplanted with human hematopoietic cells proliferating and spreading therein prepared in accordance with the process of claim 1.

12. The chimeric immunodeficient mouse of claim 11 selected from the group consisting of a bg/nu/xid mouse and a mouse bearing the SCID mutation.

13. A chimeric immunodeficient mouse deficient in T-cells and B-cells transplanted with human hematopoietic cells comprising human hematopoietic stem cells, wherein said hematopoietic stem cells are engrafted in at least murine bone marrow tissue and function by proliferating to produce progenitor cells and by differentiating into mature hematopoietic progeny.

14. The chimeric immunodeficient mouse of claim 13 selected from the group consisting of a bg/nu/xid mouse and a mouse bearing the SCID mutation.

15. A chimeric mouse of claim 13 wherein said hematopoietic cells are bone marrow cells.

16. A process for making a chimeric mouse, comprising:

i) irradiating an immunodeficient mouse which is deficient in both T-cells and B-cells before irradiation treatment to condition said mouse for transplant to permit human cell engraftment in said mouse;

ii) transplanting human leukemic cells essentially free of highly aneuploid cells by intravenous injection into said irradiated mouse; and iii) maintaining said mouse to allow said human leukemic cells to engraft and function in murine tissues to model the growth of leukemia in humans.

17. The process of claim 16, wherein said human leukemic cells proliferate, produce abnormal leukemic progeny, spread throughout the mouse and establish a human leukemia within the mouse.

18. The process of claim 16, wherein said step of irradiating said mouse comprises exposing said immunodeficient mouse to approximately 200 cGY to 950 cGY of radiation.

19. The process of claim 18, wherein said immunodeficient mouse is exposed to approximately 400 cGY.

20. The process of claim 16, wherein said immunodeficient mouse is a bg/nu/xid mouse.

21. The process of claim 16, wherein said immunodeficient mouse is a mouse bearing the SCID mutation.

22. The process of claim 16, wherein approximately $10^3$ to $10^8$ human cells are injected intravenously into said irradiated mouse.

23. A chimeric mouse transplanted with human leukemic cells proliferating and spreading therein prepared in accordance with the process of claim 16.

24. A chimeric immunodeficient mouse deficient in T-cells and B-cells transplanted with human leukemic cells wherein said leukemic cells are engrafted and function within murine tissues to model the growth of leukemia in humans.

25. The chimeric immunodeficient mouse of claim 24 selected from the group consisting of a bg/nu/xid mouse and a mouse bearing the SCID mutation.

26. The mouse of claim 24, wherein said leukemic cells proliferate, produce abnormal leukemic progeny, spread throughout the mouse and establish a human leukemia within the mouse.

* * * * *

UNITED STATES PATENT AND TRADEMARK OFFICE
CERTIFICATE OF CORRECTION

PATENT NO. : 5,994,617

DATED : November 30, 1999

INVENTOR(S) : Dick et al.

It is certified that error appears in the above-identified patent and that said Letters Patent is hereby corrected as shown below:

Title page, [56] References Cited, OTHER PUBLICATIONS, insert the following:

--Kamel-Reid et al., A Model of Human Acute Lymphoblastic Leukemia in Immune-Deficient SCID Mice, Science 246: 1597-1600 (Dec. 22, 1989)--.

Signed and Sealed this

Nineteenth Day of September, 2000

Attest:

Q. TODD DICKINSON

*Attesting Officer*      *Director of Patents and Trademarks*